United States Patent [19]
Bertoli et al.

[11] Patent Number: 5,653,966
[45] Date of Patent: Aug. 5, 1997

[54] LIPID COMPOSITION FOR COSMETIC PRODUCTS

[75] Inventors: Constantin Bertoli, Lausanne; Armand Malnoe, Dommartin, both of Switzerland

[73] Assignee: Nestec S.A., Vevey, Switzerland

[21] Appl. No.: 594,773

[22] Filed: Jan. 31, 1996

[30] Foreign Application Priority Data

Feb. 2, 1995 [EP] European Pat. Off. ............ 95101396

[51] Int. Cl.⁶ ........................... A01J 21/00; A01J 25/12
[52] U.S. Cl. ........................... 424/69; 252/106; 252/107; 424/236; 424/280; 424/284; 426/417
[58] Field of Search ............................ 424/59, 358, 69, 424/236, 280, 284, 344, 359; 252/106, 107; 426/417

[56] References Cited

U.S. PATENT DOCUMENTS

| | | | |
|---|---|---|---|
| 4,454,159 | 6/1984 | Musher | 424/358 |
| 4,526,793 | 7/1985 | Ingenbleek | 426/72 |
| 4,874,629 | 10/1989 | Chang et al. | 426/601 |
| 4,996,072 | 2/1991 | Marschner et al. | 426/417 |

FOREIGN PATENT DOCUMENTS

| | | |
|---|---|---|
| 0477825 | 4/1992 | European Pat. Off. . |
| 0581624 | 2/1994 | European Pat. Off. . |
| 193911 | 10/1985 | Japan . |

*Primary Examiner*—Terressa Mosley
*Attorney, Agent, or Firm*—Vogt & O'Donnell, LLP

[57] ABSTRACT

A lipid composition for preparation of cosmetic compositions is provided by a mixture of, by weight based upon a weight of the lipid composition, from 40% to 60% apricot kernel oil, from 10% to 20% of an oil containing palmitoleic acid, from 15% to 25% of olive oil and from 20% to 30% of rice bran oil or sesame oil or combinations thereof. Cosmetic compositions containing the lipid mixture may be anhydrous or contain water. The preparation of the lipid composition may include treating the mixture of oils with steam at a temperature of about 180° C. for about 3 hours at a rate of about 1% per hour and under a vacuum of about 1 mbar to 2 mbar for deodorizing the oils.

31 Claims, No Drawings

LIPID COMPOSITION FOR COSMETIC PRODUCTS

The present invention concerns a lipid composition intended to be used in cosmetic compositions, in particular a lipid composition having an action preparing the skin for exposure to the sun.

BACKGROUND OF THE INVENTION

Premature ageing of the epidermis is partly due to attack by UV radiation which generates free radicals.

It is known, for example from Japanese Patent Document No. 60193911, that certain vegetable oils can enter into the composition of water-resistant cosmetic products for anti-sun use containing, in addition, sun filters derived from p-amino benzoic acid.

SUMMARY OF THE INVENTION

The object of the present invention is to provide a lipid composition for cosmetic products having an anti-ageing action on the skin, namely an anti-radical, soothing and hydrating action, whilst offering natural protection against UV radiations and being naturally stabilized against oxidation, that is to say not containing added anti-oxidants, and we have unexpectedly observed that kernel oil, in addition to its cosmetic qualities, particularly its gentleness, has great material stability against oxidation.

The lipid composition according to the invention is characterized in that it contains 40 to 60% by weight of kernel oil, 10 to 20% by weight of an oil containing palmitoleic acid, 20 to 30% by weight of an oil selected from rice bran oil and sesame oil and 15 to 25% by weight of olive oil.

The present invention also provides process for the preparation of a lipid composition as defined above, wherein the oils used are refined partially by degumming, neutralization, decolorization and winterization, characterized in that the mixture of oils is deodorized under controlled conditions at about 180° C. with about 1% of live steam and under a vacuum of about 1–2 mbar for about 3 h. It is thus possible to maintain an appreciable content of unsaponifiable matter and in particular to conserve tocopherols.

DETAILED DESCRIPTION OF THE INVENTION

In the context of the composition of the present invention, the kernel oil of the composition is, in particular, apricot kernel oil.

Avocado oil or macadamia oil may be cited as an oil containing palmitoleic acid, an acid which is found in sebum, in particular in young subjects. Avocado oil is preferred for its good penetration and from the fact that it contains compounds capable of acting as a natural filter for UV rays.

The composition may contain rice bran oil which is particularly rich in gamma-oryzanol having an anti-oxidant activity.

The composition may contain, as a partial or total replacement for rice bran oil, sesame oil, certain constituents of which specifically inhibit delta 5 desaturase, the enzyme responsible for the biotransformation of dihomogamma-linoleic acid (DHGLA) into arachidonic acid (AA). It is thus likely to have an anti-inflammatory action in as much as the formation of products derived from AA such as, for example, leucotriene B4, which is pro-inflammatory, should be reduced, to the advantage of products derived from DHGLA, for example series 1 prostaglandins having an anti-inflammatory activity.

The composition contains an appreciable quantity of oleic acid which confers good stability to oxidation and photo-oxidation on the lipid mixture, which prevents the formation of active oxygenated radicals.

The composition contains oils providing essential fatty acids of the n-6 family, low in n-3 fatty acids, to take into account the greater sensitivity of those of the n-3 family to oxidation.

Thus, the composition contains an appreciable quantity of linoleic acid. This acid is a constituent of ceramides which play an important role as a barrier against dehydration of the epidermis. Linoleic acid proves to be equally active against cellular hyperproliferation associated with a deficiency in essential fatty acids.

The average composition in fatty acids of triglycerides in the final composition is as follows:

| Fatty acids | | % by weight | | % by weight |
|---|---|---|---|---|
| C16:0 | | 10–15 | preferably | <13.5 |
| C16:1, | n-7 | 1–2 | " | <1.5 |
| C18:0 | | 1–2 | " | <1.5 |
| C18:1, | n-9 | 50–65 | " | <63 |
| C18:2, | n-6 | 20–30 | " | <28 |
| C18:3, | n-3 (alpha) | 0.3–1 | " | <0.5 |
| C20:0 | | <1 | " | <0.3 |
| C20:1 | | <2 | " | <1.5 |

On the basis of their respective compositions in fatty acids and in natural anti-oxidant constituents, the following mixtures of oils are preferred:

| Oil | % by weight | | % by weight |
|---|---|---|---|
| Apricot kernel oil | 40–60 | preferably | 40 |
| Avocado oil | 10–20 | " | 20 |
| Rice bran oil | 20–30 | " | 20 |
| Olive oil | 15–25 | " | 20 |

The lipid composition according to the invention may be, advantageously, used in various aqueous or anhydrous cosmetic compositions for treatment of the skin, such as fluids, creams and lotions for the face, hands and body, creams and anti-sun lotions.

The cosmetic composition in question may be in particular in the form of a solution, a water-in-oil emulsion, particularly a cream, or an oil-in-water emulsion particularly a lotion, or, a suspension or an aerosol.

As anhydrous cosmetic compositions incorporating the lipid composition according to the invention, reference may be made to body oils, anhydrous balms, anti-sun oils and lipsticks.

In such a cosmetic composition, the lipid composition according to the invention may represent 1 to 80%, preferably 5 to 60% by weight.

Such a cosmetic composition generally includes, in suitable quantities, additives such as, for example, emulsifiers, anti-perspirants, stabilizers, UV filters, preservatives, perfumes, colorants or emollients, waxes, pearl agents and inorganic or organic fillers.

EXAMPLES

The following examples illustrate the invention. In these, percentages and parts are given by weight except where indicated to the contrary.

Example 1

Preparation of a Mixture of Oils

The following partially refined oils were mixed with stirring under nitrogen in the proportions indicated.

| Oil | % by weight | | % by weight |
| --- | --- | --- | --- |
| Apricot kernel oil | 40–60 | preferably | 40 |
| Avocado oil | 10–20 | " | 20 |
| Rice bran oil | 20–30 | " | 20 |
| Olive oil | 15–25 | " | 20 |

The oils were mixed in the proportions indicated above in a stainless steel reactor provided with a double walled system with fluid circulation to keep the temperature constant and a variable speed stirrer, whilst avoiding temperatures greater than 30° C.

The mixture was then heated to 65° C. and treated with 0.3% of 50% citric acid, 2 to 3% of water was then added and the precipitated gums were separated by centrifuging.

The degummed mixture was then put into contact with 1% hydrated amorphous silica gel (TRISYL) and 0.5% hydrated amorphous silica gel (Trisyl 300(R)) at 80°–85° C. for 20 min under a vacuum of 50–80 mbar.

The mixture was finally deodorized at 180° C. for 3 hours by steam entrainment with 1% of steam per hour.

The mixture had an induction time of 22.7 h in the Rancimat test at 100° C.

Example 2

Anhydrous balm

| Ingredient | % |
| --- | --- |
| Lanolin | 35 |
| Hydrogenated lanolin | 30 |
| Ozokerite | 3 |
| Lipid composition according to example 1 | 20 |
| Cyclopentadimethylsiloxane | 12 |

The preceding anhydrous product was obtained by mixing the constituents at 70° C. and then cooling, while stirring, until room temperature was reached.

Example 3

Lipstick (anhydrous)

| Ingredients | % |
| --- | --- |
| Fatty alcohol esters C8–C10 | 26 |
| Ozokerite | 10 |
| Carnauba wax | 3 |
| Bees wax | 3 |
| Pigment | 9 |
| Perfume | 0.1 |
| Castor oil | qsp 100 |
| Lipid composition of example 1 | 6 |

The pigments were sieved. The constituents were then mixed at 70° C., except for the perfume. The mixture was left to cool to 35° C. with stirring and the perfume was then added. The preparation was finally transferred to a triple roll mill.

Example 4

Make-up foundation

| Ingredients | % |
| --- | --- |
| Lipid composition of example 1 | 4 |
| Mixture of glyceryl mono-stearate and di-stearate, stearic acid and glycerine (40/50/5/5) | 3.3 |
| Mixture of lanolin alcohol and liquid paraffin (15/85) | 3 |
| Glyceryl mono-di-iso-stearate | 1.8 |
| Isopropyl palmitate | 5 |
| ethyl-2-hexyl palmitate | 5 |
| Titanium oxide | 8.31 |
| Brown iron oxide | 0.73 |
| Yellow iron oxide | 1.7 |
| Black iron oxide | 0.26 |
| Propyl p-hydroxybenzoate | 0.1 |
| Methyl p-hydroxybenzoate | 0.1 |
| Perfume | 0.3 |
| Triethanolamine | 1.2 |
| Hydrated magnesium aluminium silicate | 1.5 |
| Sodium carboxymethylcellulose | 0.14 |
| Cyclopentadimethylsiloxane | 8 |
| Glycerine | 3 |
| Sterilized demineralized water | qsp 100 |
| Propylene glycol | 3 |
| Stearic acid | 2.4 |

The pigments were blended and sieved and they were then incorporated in the oily phase, previously heated to 70° C. The sodium carboxymethylcellulose was dispersed separately in water. When the solution was homogeneous, the other components of the aqueous phase were added and the mixture was heated to 75° C. The two phases were then emulsified with rapid homogenization. The emulsion was allowed to cool with stirring, the perfume and triethanolamine were added at 35° C. and homogenization was then carried out. The preparation was then transferred to a triple roll mill.

Example 5

Moisturising protective body lotion

| Ingredients | % |
| --- | --- |
| Polysorbate 60 | 0.8 |
| Perfume | 0.3 |
| Glycerol stearate and PEG 100 stearate | 1 |
| Hydrogenated polyisobutene | 2 |
| Lipid composition of example 1 | 8 |
| Stearic acid | 1 |
| Glycerine | 3 |
| Carbopol 941 | 0.3 |
| Triethanolamine | 0.3 |
| Water + preservative | qsp 100 |

The Carbopol 941 was dispersed in water. When the solution was homogeneous, the other components of the aqueous phase were added and the mixture was heated to 75° C. The constituents of the oily phase were mixed separately at 70° C. The two phases were then emulsified with rapid homogenization. The mixture was allowed to cool with stirring and the perfume, triethanolamine and preservative were added at 35° C., and homogenization was then carried out. The preparation was allowed to cool to room temperature and packaged.

Example 6

Protective care fluid

| Ingredients | % |
| --- | --- |
| Methyl glucose sesquistearate | 2 |
| Lipid composition of example 1 | 2 |
| Cyclomethicone | 13 |
| Perfume | 0.2 |
| PEG 20 methyl glucose sesquistearate | 2 |
| Xanthan gum | 0.2 |
| Acid polyacrylamide and C13–C14 - isoparaffin and laureth 7 | 0.8 |
| Water + preservatives | qsp 100 |

The xanthan gum was dispersed in water at 75° C. The constituents of the oily phase were mixed separately at 70° C. The two phases were then emulsified under rapid homogenization. The mixture was allowed to cool with stirring, the perfume and preservative was added at 35° C. and homogenization was then carried out. The preparation was then allowed to cool to room temperature and packaged.

Example 7

Protective care cream, oil-in-water emulsion

| Ingredients | % |
| --- | --- |
| PEG 20 stearate | 1 |
| Glyceryl stearate and PEG 100 Stearate | 1 |
| Stearic acid | 1 |
| Stearyl alcohol | 2 |
| Lipid composition of example 1 | 20 |
| Soya protein hydrolysate | 0.2 |
| Glycerine | 3 |
| Carbopol 941 | 0.4 |
| Triethanolamine | 0.4 |
| Water + preservative | qsp 100 |

The Carbopol 941 was dispersed in water. When the solution was homogeneous, the other components of the aqueous phase were added and the mixture was heated to 70° C. The constituents of the oily phase were mixed separately at 75° C. Emulsification of the two phases was then carried out under rapid homogenization. The mixture was then allowed to cool with stirring and the perfume was added at 35° C., and homogenization was then carried out. The preparation was allowed to cool to room temperature and packaged.

Example 8

Care cream, water-in-oil emulsion

| Ingredients | % |
| --- | --- |
| Sorbitan mono isostearate | 5 |
| Microcrystalline wax | 1 |
| Lipid composition of example 1 | 19 |
| Fatty acid esters in C8–C10 and fatty alcohols in C12–C18 | 1 |
| Modified Montmorillonite gel and neutral oil (triglycerides of caprylic and capric acids) | 5 |
| Propylene glycol | 3 |
| Water + preservative | qsp 100 |

The constituents of the oily phase were mixed at 75° C. The constituents of the aqueous phase were mixed separately at 70° C. After emulsification of the two phases under rapid homogenization, the mixture was allowed to cool with stirring to room temperature and packaged.

Example 9

Sun cream, water-in-oil emulsion

| Ingredients | % |
| --- | --- |
| 4-(1,1-dimethylethyl)-4'-methoxydibenzoylmethane (PARSOL 1789) | 1.5 |
| p-methylbenzylidene camphor (EUSOLEX 6300) | 4.5 |
| Mixture of cetylstearyl alcohol and cetylstearyl alcohol oxyethylenated with 33 moles of ethylene oxide | 7.3 |
| Mixture of glycerol mono- and distearate | 2.1 |
| Mixture of oils of example 1 | 31.4 |
| Polydimethyl siloxane | 1.6 |
| Cetyl alcohol | 1.6 |
| Water | qsp 100 |

This emulsion was prepared according to conventional techniques by dissolving the filters in the oily phase containing emulsifying agents, while heating this oily phase to 80°–85° C. and whilst adding water, previously heated to 80° C., with vigorous stirring.

We claim:

1. In a process for refining an oil wherein an oil is subjected to degumming, neutralization, decolorizing, winterizing and deodorizing, the improvements comprising:

treating a mixture of oils with steam at a temperature of about 180° C. for about 3 hours at a rate of about 1% per hour and under a vacuum of about 1 mbar to 2 mbar for deodorizing the oils to obtain a lipid composition wherein the mixture of oils comprises by weight based upon a weight of the mixture from 40% to 60% of kernel oil, from 10% to 20% of an oil containing palmitoleic acid, from 15% to 25% of olive oil and from 20% to 30% of an oil selected from the group consisting of rice bran oil and sesame oil and combinations thereof.

2. A process according to claim 1 wherein the kernel oil is apricot kernel oil.

3. A process according to claim 1 wherein the oils comprise an oil selected from the group consisting of avocado oil and macadamia oil.

4. A process according to claim 2 wherein the oils comprise an oil selected from the group consisting of avocado oil and macadamia oil.

5. A process according to claim 4 wherein the oils comprise rice bran oil.

6. The lipid composition product of the process of claim 2.

7. The lipid composition product of the process of claim 5.

8. A lipid composition comprising a mixture of, by weight based upon a weight of the composition, from 40% to 60% apricot kernel oil, from 10% to 20% of an oil containing palmitoleic acid, from 15% to 25% olive oil and from 20% to 30% of an oil selected from the group consisting of rice bran oil and sesame oil and combinations thereof.

9. A lipid composition according to claim 8 wherein the mixture comprises avocado oil.

10. A lipid composition according to claim 8 wherein the mixture comprises macadamia oil.

11. A lipid composition according to claim 9 wherein the mixture comprises rice bran oil.

12. A lipid composition according to claim 9 wherein the mixture comprises sesame oil.

13. A lipid composition according to claim 10 wherein the mixture comprises rice bran oil.

14. A lipid composition according to claim 10 wherein the mixture comprises sesame oil.

15. A lipid composition according to claim 11 wherein the mixture comprises sesame oil.

16. A lipid composition according to claim 8 wherein the oils are in amounts so that the lipid composition has a triglyceride fatty acid composition comprising:

| Fatty acids | % by weight |
| --- | --- |
| C16:0 | 10–15 |
| C16:1, n-7 | 1–2 |
| C18:0 | 1–2 |
| C18:1, n-9 | 50–65 |
| C18:2, n-6 | 20–30 |
| C18:3, n-3 (alpha) | 0.3–1 |

17. A cosmetic composition comprising a cosmetic constituent and lipids comprising, by weight based upon a weight of the lipids, from 40% to 60% apricot kernel oil, from 10% to 20% of an oil containing palmitoleic acid, from 15% to 25% olive oil and from 20% to 30% of an oil selected from the group consisting of rice bran oil and sesame oil and combinations thereof.

18. A cosmetic composition according to claim 17 wherein the lipids comprise avacado oil.

19. A cosmetic composition according to claim 17 wherein the lipids comprise macadamia oil.

20. A cosmetic composition according to claim 18 wherein the lipids comprise rice bran oil.

21. A cosmetic composition according to claim 18 wherein the lipids comprise sesame oil.

22. A cosmetic composition according to claim 19 wherein the lipids comprise rice bran oil.

23. A cosmetic composition according to claim 19 wherein the lipids comprise sesame oil.

24. A cosmetic composition according to claim 20 wherein the lipids comprise sesame oil.

25. A cosmetic composition according to claim 17 wherein the oils are in amounts so that the lipids provide a triglyceride fatty acid composition comprising:

| Fatty acids | % by weight |
| --- | --- |
| C16:0 | 10–13.5 |
| C16:1, n-7 | 1–1.5 |
| C18:0 | 1–1.5 |
| C18:1, n-9 | 50–63 |
| C18:2, n-6 | 20–28 |
| C18:3, n-3 (alpha) | 0.3–0.5. |

26. A cosmetic composition according to claim 17 wherein the lipids comprise from 1% to 80% of the composition.

27. A cosmetic composition according to claim 17 wherein the composition is an anhydrous composition.

28. A cosmetic composition according to claim 27 wherein the composition has a form selected from the group consisting of a balm and a lipstick.

29. A cosmetic composition according to claim 17 further comprising water.

30. A cosmetic composition according to claim 29 wherein the composition has a form selected from the group consisting of a solution, a water-in-oil emulsion, an oil-in-water emulsion, a suspension and an aerosol.

31. A cosmetic composition according to claim 17 wherein the cosmetic constituent comprises at least one substance selected from the group consisting of an emulsifier, an anti-perspirant, a UV filter, a perfume, a colorant, an emollient, a pearl agent, and a wax.

* * * * *